United States Patent
Fairneny et al.

(10) Patent No.: US 9,168,120 B2
(45) Date of Patent: Oct. 27, 2015

(54) MEDICAL DEVICE AND METHODS OF DELIVERING THE MEDICAL DEVICE

(75) Inventors: Ty Fairneny, Hopkinton, MA (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 272 days.

(21) Appl. No.: 13/606,883

(22) Filed: Sep. 7, 2012

(65) Prior Publication Data

US 2013/0066145 A1 Mar. 14, 2013

Related U.S. Application Data

(60) Provisional application No. 61/532,809, filed on Sep. 9, 2011.

(51) Int. Cl.
*A61F 2/00* (2006.01)
*A61F 13/00* (2006.01)

(52) U.S. Cl.
CPC .................................. *A61F 2/0045* (2013.01)

(58) Field of Classification Search
CPC .................. A61F 2/0045; A61B 2017/00805; A61B 17/0401
USPC .................................. 600/37, 29, 30; 606/41
See application file for complete search history.

(56) References Cited

U.S. PATENT DOCUMENTS

| | | |
|---|---|---|
| 669,034 A | 2/1901 | Manly |
| 2,687,131 A | 8/1954 | Raiche |
| 3,123,077 A | 3/1964 | Alcamo |
| 4,083,369 A | 4/1978 | Sinnreich |
| 4,324,331 A | 4/1982 | Ignasiak |
| 4,792,336 A | 12/1988 | Hlavacek et al. |
| 4,919,667 A | 4/1990 | Richmond |
| 4,998,912 A | 3/1991 | Scarbrough et al. |
| 5,013,292 A | 5/1991 | Lemay |
| 5,082,112 A | 1/1992 | Dunklee |
| 5,112,344 A | 5/1992 | Petros |

(Continued)

FOREIGN PATENT DOCUMENTS

| | | |
|---|---|---|
| DE | 10056169 A1 | 6/2002 |
| EP | 0088714 A1 | 9/1983 |

(Continued)

OTHER PUBLICATIONS

Leron, E. et al., "Sacrohysteropexy with synthetic mesh for the management of uterovaginal prolapse", British Journal of Obstetrics and Gynaecology, 108.3, 2001, pp. 629-633.

(Continued)

*Primary Examiner* — Christine H Matthews
*Assistant Examiner* — Sunita Reddy
(74) *Attorney, Agent, or Firm* — Brake Hughes Bellermann LLP (57) ABSTRACT

The present invention discloses a medical device and a method of placing the medical device within a patient's body. The medical device includes a support member, a first elongate member, a second elongate member and a coupling member. The first elongate member and the second elongate member extend from the support member. The coupling member includes a first portion and a second portion. The first portion of the coupling member is coupled to a distal end portion of the first elongate member and the second portion of the coupling member is coupled to a distal end portion of the second elongate member.

20 Claims, 8 Drawing Sheets

(56) References Cited

U.S. PATENT DOCUMENTS

| | | |
|---|---|---|
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,364,408 A | 11/1994 | Gordon |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,464,409 A | 11/1995 | Mohajer |
| 5,485,917 A | 1/1996 | Early |
| 5,527,341 A | 6/1996 | Gogolewski et al. |
| 5,534,008 A | 7/1996 | Acksel |
| 5,540,704 A | 7/1996 | Gordon et al. |
| 5,562,689 A | 10/1996 | Green et al. |
| 5,569,283 A | 10/1996 | Green et al. |
| 5,575,800 A | 11/1996 | Gordon |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,871,488 A | 2/1999 | Tovey et al. |
| 5,899,909 A | 5/1999 | Claren et al. |
| 5,922,826 A | 7/1999 | Kuze et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A | 1/2000 | Kardjian |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,195,646 B1 | 2/2001 | Grosh et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar et al. |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac et al. |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |

(56) References Cited

U.S. PATENT DOCUMENTS

| | | |
|---|---|---|
| 7,402,133 B2 | 7/2008 | Chu et al. |
| 7,413,540 B2 | 8/2008 | Gellman et al. |
| 7,527,588 B2 | 5/2009 | Zaddem |
| 7,878,970 B2 | 2/2011 | Goldberg |
| 2001/0023356 A1 | 9/2001 | Raz et al. |
| 2001/0049467 A1 | 12/2001 | Lehe et al. |
| 2002/0010457 A1 | 1/2002 | Duchon et al. |
| 2002/0028980 A1 | 3/2002 | Thierfelder et al. |
| 2002/0099259 A1 | 7/2002 | Anderson et al. |
| 2002/0128670 A1 | 9/2002 | Ulmsten et al. |
| 2002/0133236 A1 | 9/2002 | Rousseau |
| 2002/0143234 A1 | 10/2002 | LoVuolo |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0023138 A1 | 1/2003 | Luscombe |
| 2003/0023250 A1 | 1/2003 | Watschke et al. |
| 2003/0055313 A1 | 3/2003 | Anderson et al. |
| 2003/0078604 A1 | 4/2003 | Walshe |
| 2003/0125715 A1 | 7/2003 | Kuehn et al. |
| 2003/0149334 A1 | 8/2003 | Ulmsten et al. |
| 2003/0176762 A1 | 9/2003 | Kammerer |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 | 12/2003 | Benderev |
| 2003/0233107 A1 | 12/2003 | Gellman et al. |
| 2003/0233108 A1 | 12/2003 | Gellman et al. |
| 2004/0006353 A1 | 1/2004 | Bosley et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1 | 2/2004 | Gellman et al. |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0073234 A1 | 4/2004 | Chu et al. |
| 2004/0087970 A1 | 5/2004 | Chu et al. |
| 2004/0106847 A1 | 6/2004 | Benderev |
| 2004/0116944 A1 | 6/2004 | Chu et al. |
| 2004/0133217 A1 | 7/2004 | Watschke |
| 2004/0138747 A1 | 7/2004 | Kaladelfos |
| 2004/0181243 A1 | 9/2004 | Chu et al. |
| 2004/0186515 A1 | 9/2004 | Rosenblatt |
| 2004/0225181 A1 | 11/2004 | Chu et al. |
| 2004/0230206 A1 | 11/2004 | Gellman et al. |
| 2004/0231678 A1 | 11/2004 | Fierro |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0250978 A1 | 11/2005 | Kammerer |
| 2005/0256366 A1 | 11/2005 | Chu |
| 2005/0256530 A1 | 11/2005 | Petros |
| 2005/0261545 A1 | 11/2005 | Gellman et al. |
| 2005/0261547 A1 | 11/2005 | Bouffier |
| 2005/0277807 A1 | 12/2005 | MacLean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0041263 A1 | 2/2006 | Chu et al. |
| 2006/0052801 A1 | 3/2006 | Dreyfuss et al. |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229596 A1 | 10/2006 | Weiser et al. |
| 2006/0264698 A1 | 11/2006 | Kondonis et al. |
| 2007/0161849 A1 | 7/2007 | Goldberg et al. |
| 2007/0173864 A1 | 7/2007 | Chu |
| 2007/0270890 A1 | 11/2007 | Miller |
| 2007/0276358 A1 | 11/2007 | Barzell et al. |
| 2008/0234543 A1 | 9/2008 | Goldwasser |
| 2009/0171140 A1 | 7/2009 | Chu |
| 2010/0130814 A1* | 5/2010 | Dubernard ................ 600/30 |
| 2010/0152530 A1 | 6/2010 | Timmer et al. |
| 2011/0098527 A1 | 4/2011 | Goldberg |
| 2011/0112357 A1* | 5/2011 | Chapman et al. ............ 600/37 |
| 2012/0059217 A1 | 3/2012 | Goldberg |
| 2012/0136324 A1* | 5/2012 | Hanuka et al. ............. 604/318 |

FOREIGN PATENT DOCUMENTS

| | | |
|---|---|---|
| EP | 0141589 A1 | 5/1985 |
| EP | 0299158 A1 | 1/1989 |
| EP | 0362146 A1 | 4/1990 |
| EP | 0412664 A1 | 2/1991 |
| EP | 0567130 A1 | 10/1993 |
| EP | 0774240 A1 | 5/1997 |
| EP | 1201189 A2 | 5/2002 |
| EP | 1508305 A2 | 2/2005 |
| EP | 1520554 A2 | 4/2005 |
| EP | 1609439 A1 | 12/2005 |
| FR | 2785521 A1 | 5/2000 |
| FR | 2852817 A1 | 10/2004 |
| FR | 2852818 A1 | 10/2004 |
| FR | 2871365 A1 | 12/2005 |
| GB | 670349 | 4/1952 |
| JP | 06114067 A2 | 4/1994 |
| JP | 08117239 A2 | 5/1996 |
| MX | PA04008407 A | 12/2005 |
| WO | 96/09796 A2 | 4/1996 |
| WO | 96/39948 A1 | 12/1996 |
| WO | 98/35616 A1 | 8/1998 |
| WO | 98/35632 A1 | 8/1998 |
| WO | 98/43545 A1 | 10/1998 |
| WO | 99/37216 A1 | 7/1999 |
| WO | 00/09039 A1 | 2/2000 |
| WO | 00/74613 A1 | 12/2000 |
| WO | 01/06951 A1 | 2/2001 |
| WO | 01/52135 A1 | 7/2001 |
| WO | 02/31681 A1 | 4/2002 |
| WO | 02/32284 A2 | 4/2002 |
| WO | 02/38079 A2 | 5/2002 |
| WO | 02/058563 A1 | 8/2002 |
| WO | 02/062237 A1 | 8/2002 |
| WO | 02/078571 A1 | 10/2002 |
| WO | 03/068107 A1 | 8/2003 |
| WO | 03/073960 A1 | 9/2003 |
| WO | 03/092546 A2 | 11/2003 |
| WO | 03/096928 A1 | 11/2003 |
| WO | 03/096929 A1 | 11/2003 |
| WO | 2004/012626 A1 | 2/2004 |

(56) References Cited

FOREIGN PATENT DOCUMENTS

| WO | 2004/016196 | A2 | 2/2004 |
|----|-------------|----|--------|
| WO | 2004/045457 | A1 | 10/2004 |
| WO | 2004/091442 | A2 | 10/2004 |
| WO | 2004/091443 | A2 | 10/2004 |
| WO | 2005/051204 | A1 | 6/2005 |
| WO | 2005/122721 | A2 | 12/2005 |
| WO | 2005/122954 | A1 | 12/2005 |
| WO | 2006/046950 | A1 | 5/2006 |
| WO | 2007/014240 | A1 | 2/2007 |
| WO | 2007/016698 | A2 | 2/2007 |
| WO | 2007/019374 | A2 | 2/2007 |
| WO | 2007038589 | A2 | 4/2007 |
| WO | 2007/087132 | A1 | 8/2007 |
| WO | 2009/038781 | A1 | 3/2009 |
| WO | 2009/102945 | A2 | 8/2009 |
| WO | 2012/030834 | A2 | 3/2012 |
| WO | 2012/030834 | A3 | 3/2012 |

OTHER PUBLICATIONS

"Capio® CL Transvaginal Suture Capturing Device", Transvaginal Suture Fixation to Cooper's Ligament for Sling Procedures, Boston Scientific, 2000, 4 pages.

"Capio® Open Access and Standard Suture Capturing Devices", Reach, Throw and Capture: One Step. One Device., Boston Scientific, printed on Apr. 7, 2006, 2 pages.

"Capio® RP Suture Device", Boston Scientific, printed on Apr. 7, 2006, 1 page.

Hardiman, et al, "Sacrospinous Vault Suspension and Abdominal Colposacropexy: Success Rates and Complications", Section of Urogynecology, Department of Obstetrics and Gynecology, University of Toronto, Mount Sinai Hospital, Sep. 18, 1995, 5 pages.

Pohl, et al, "Bilateral Transvaginal Sacrospinous Colpopexy: Preliminary Experience", 23rd Annual Meeting of the Society of Gynecologic Surgeons, Feb. 24-26, 1997, 7 pages.

Shah, et al, "Short-Term Outcome Analysis of Total Pelvic Reconstruction With Mesh: The Vaginal Approach", The Journal of Urology, vol. 171, Jan. 2004, pp. 261-263.

\* cited by examiner

MEDICAL DEVICE AND METHODS OF DELIVERING THE MEDICAL DEVICE

CROSS-REFERENCE TO RELATED APPLICATION

This application is a Nonprovisional of, and claims priority to, U.S. Patent Application No. 61/532,809, filed Sep. 9, 2011, entitled "A MEDICAL DEVICE AND METHODS OF DELIVERING THE MEDICAL DEVICE", which is incorporated by reference herein in its entirety.

BACKGROUND

1. Field

The present invention generally relates to implants and more particularly to bodily implants and their methods of delivery and placement into a patient's body for the treatment of pelvic floor repair.

2. Description of the Related Art

Genital prolapse or pelvic floor prolapse is the protrusion of pelvic organs into or out of the vaginal canal. Pelvic floor prolapse affects many women and many of them undergo at least one reconstructive pelvic surgery in their lifetime. Many of the cases may be the result of damage to the vaginal and pelvic support tissue by stretching or tearing of the connective tissue within the pelvic space due to childbirth, age, obesity, post-menopausal conditions or chronically elevated intra-abdominal pressure. The results are the distention of organs such as the bladder and rectum, into the vagina, as well as various stages of vaginal avulsion.

Surgical therapy may be performed for the treatment of pelvic organ prolapse. Such surgeries for prolapse treatment may include plication of the torn connective tissues and re-suspension of the vagina. Some traditional suspension techniques include utero-sacral suspension and sacrospinus ligament suspension. Some procedures for vaginal suspension include sacrocolpopexy, where the vagina is suspended to the sacral promontory with an implanted graft material.

Hysterectomy may be performed before conducting sacrocolpopexy. It involves surgical removal of the uterus so that the bodily implant can be attached properly to the anterior and posterior vaginal walls. Hysterectomy may be total (removal of the cervix and the uterus) or partial (removal of the uterus while leaving the cervix intact). This may be an undesirable outcome of pelvic floor repair as removal of the uterus can create many complications and render the patient unable to bear children. Therefore, many women do not prefer removal of the uterus.

Therefore, a medical device and a method for placing the medical device within the patient's body is required that overcomes the need of removal of the uterus through either total or partial hysterectomy.

SUMMARY

The present invention discloses a medical device and a method of placing the medical device within a patient's body. The medical device includes a support member, a first elongate member, a second elongate member and a coupling member. The first elongate member and the second elongate member extend from the support member. The first elongate member and the second elongate member include a proximal end portion and a distal end portion. The proximal end portion of the first elongate member is configured to be attached to the support member and the distal end portion of the first elongate member is configured to be attached around a portion of a uterus. The proximal end portion of the second elongate member is configured to be attached to the support member and the distal end portion of the second elongate member is configured to be attached around a portion of a uterus. The coupling member includes a first portion and a second portion. The first portion of the coupling member is coupled to the distal end portion of the first elongate member and the second portion of the coupling member is coupled to the distal end portion of the second elongate member. The first portion of the coupling member and the second portion of the coupling member are further configured to be coupled together.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating uterine prolapse. However, the invention may be equally employed for other treatment purposes such as pelvic organ prolapse. As described below in various illustrative embodiments, the invention provides systems, methods, and devices employing an improved medical device configured to be implanted within a patient's body to support pelvic organs for the treatment of pelvic prolapse.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, or any other mammal.

Figure 1:
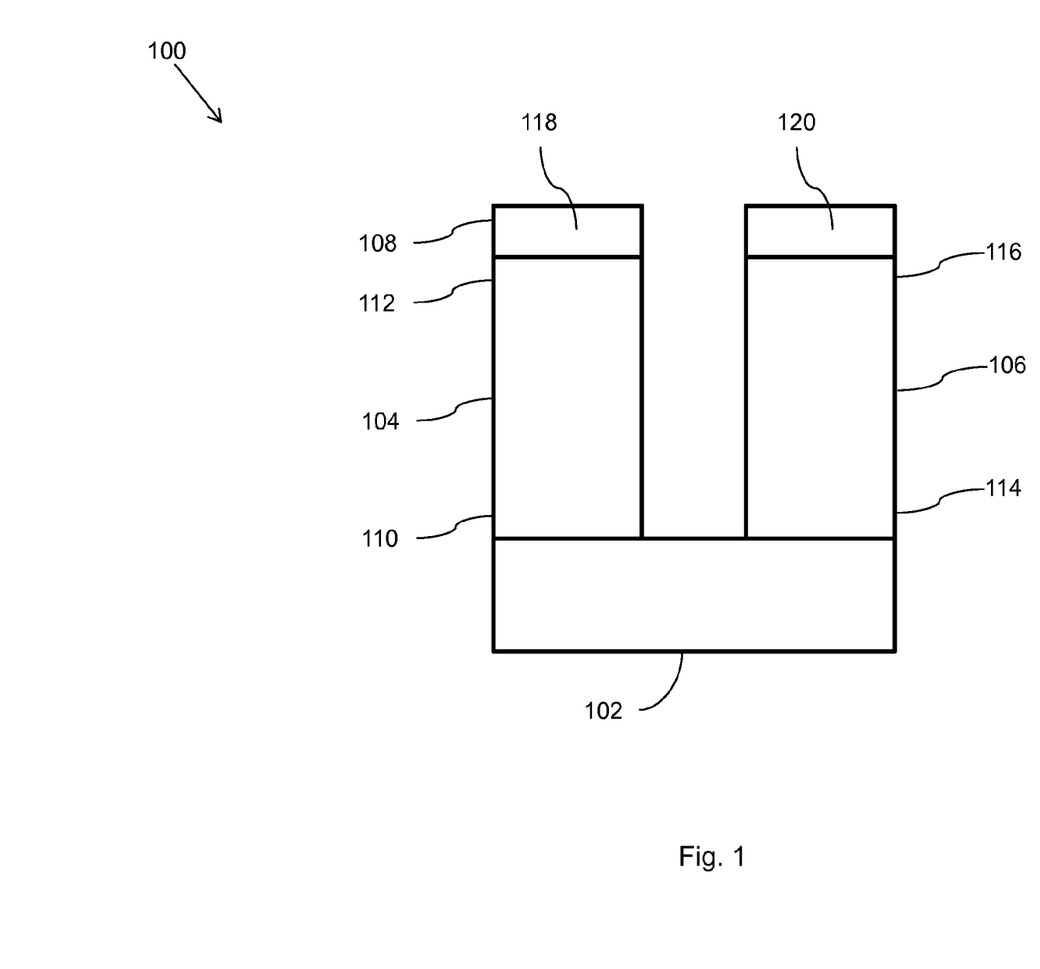
FIG. 1 is a schematic diagram of a medical device configured to be placed within a patient's body, in accordance with an embodiment of the present invention.

FIG. 1 is a schematic diagram of a medical device 100 configured to be implanted within a patient's body, in accordance with an embodiment of the present invention. The medical device 100 includes a support member 102, a first elongate member 104, a second elongate member 106 and a coupling member 108. The first elongate member 104 includes a proximal end portion 110 and a distal end portion 112. Similarly, the second elongate member 106 includes a proximal end portion 114 and a distal end portion 116. The coupling member 108 includes a first portion 118 and second portion 120.

The support member 102 is configured to be placed within a patient's body such that the support member 102 disposed adjacent a first bodily portion. In some embodiments, the support member 102 is attached or stitched to the first bodily portion. In some embodiments, the first bodily portion is a portion of an anterior vaginal wall of the patient such that the support member 102 is attached or stitched to the portion of the anterior vaginal wall. In other embodiments, the first bodily portion is a portion of a posterior vaginal wall of the patient such that the support member 102 is configured to support the portion of the posterior vaginal wall.

The support member 102 can be of different shapes, sizes, and configurations depending on the indented use of the medical device 100 and location of its placement within the body of the patient. In some embodiments, the support member 102 can be substantially rectangular, square, oval, or elliptical. The support member 102 can be shaped and sized in conformation to the portions of the vaginal walls of the patient where it is attached or stitched. In accordance with several embodiments, the support member 102 may be configured to conform to the shape of the body of the patient. For example, the support member 102 may be placed in a crescent shape, such as in the shape of a crescent moon, to help it conform to the shape of the anterior wall of the vagina.

The first elongate member 104 extends from the support member 102. The proximal end portion 110 of the first elongate member 104 is attached to the support member 102 and the distal end portion 112 of the first elongate member 104 is configured to be attached around a second bodily portion. In some embodiments, the second bodily portion is a portion of a uterus of the patient such that the distal end portion 112 of the first elongate member 104 is wrapped around the portion of the uterus. In other embodiments, the second bodily portion is a portion of a cervix of the patient such that the distal end portion 112 of the first elongate member 104 is wrapped around the portion of the cervix of the patient. In accordance with some embodiments, the wrapped first elongate member 204 can be stitched around the portion of the uterus or the cervix. Thus the stitched first elongate member 204 provides a support to the uterus and/or the cervix.

The second elongate member 106 extends from the support member 102. The proximal end portion 114 of the second elongate member 106 is attached to the support member 102 and the distal end portion 116 of the second elongate member 106 is configured to be attached around a third bodily portion. In some embodiments, the third bodily portion is a portion of a uterus of the patient such that the distal end portion 116 of the second elongate member 106 is wrapped around the portion of the uterus. In other embodiments, the third bodily portion is a portion of a cervix of the patient such that the distal end portion 116 of the second elongate member 106 is wrapped around the portion of the cervix. In accordance with some embodiments, the wrapped second elongate member 204 can be stitched around the portion of the uterus or the cervix. Thus the stitched second elongate member 204 provides a support to the uterus and/or the cervix. In some embodiments, the second bodily portion and the third bodily portion are same. In some other embodiments, the second bodily portion and the third bodily portion are different.

The first elongate member 104 and second elongate member 106 can be of a variety of different shapes, sizes, and configurations depending on the indented use of the medical device 100 and location of its placement within the body of the patient. In some embodiments, the first elongate member 104 and the second elongate member 106 can be substantially planar, cylindrical, tubular, vasiform, cannular and the like.

In some embodiments, the first elongate member 104 and the second elongate member 106 are integral portions of the support member 102 such that the support member, the first elongate member 104, and the second elongate member form a single integral structure. In other embodiments, the first elongate member 104 and the second elongate member 106 are removably or fixedly coupled to the support member 102 by an operator. The first elongate member 104 and the second elongate member 106 may extend from any location of the support member 102 such that the medical device 100 comfortably supports and retains the prolapsed organ of the patient. In some cases, the first elongated member 104 and the second elongated member 106 can be coupled to the support member 102 at two symmetric locations on either side of a central axis of the support member 102. In other cases, the first elongate member 104 and the second elongate member 106 can be coupled to the support member 102 at two diametrically opposite locations.

In an embodiment, the support member 102, the first elongate member 104, and the second elongate member 106 includes a mesh body that can be made from a biological material or a cadaveric tissue such as stem cells, natural xenograft material, collagen growth factors, and the like. In another embodiment, the support member 102, the first elongate member 104 and the second elongate member 106 includes a mesh body that may be made up of synthetic material such as a plastic, polypropylene mesh or other plastic materials. In some embodiments, the support member 102, the first elongate member 104, and the second elongate member 106 are made of a flexible material. In other embodiments, the support member 102, the first elongate member 104, and the second elongate member 106 are made of an elastic material. In some embodiments, the support member 102, the first elongate member 104, and the second elongate member 106 are formed of the same material. In certain other embodiments, the support member 102, the first elongate member 104, and the second elongate member 106 are formed of different materials. For example, the support member 102 can be formed from a first biocompatible material, and the first elongate member 104 and the second elongate member 106 can be formed from a second biocompatible material different than the first biocompatible material.

In some embodiments, the support member 102, the first elongate member 104, and the second elongate member 106 are formed of a material that allows tissue in-growth after implantation. In some embodiments, the elastic and flexible synthetic material employed in the support member 102, the first elongate member 104, and the second elongate member 106 may allow stretching of the medical device 100 without abdominal straining. Additionally, the medical device 100 may be coated, impregnated, or formed with one or more drugs to be eluted to an adjacent tissue, in accordance with several other embodiments.

The support member 102, the first elongate member 104, and the second elongate member 106 can have a variety of sizes (length, width, and thickness) depending on the intended use of a particular medical device such as the medical device 100 and the intended site of implantation. For example, the size of the support member 102 can depend on the size of the vaginal wall. Similarly, the size of the first elongate member 104 and the second elongate member 106 can have a length such that the support member 102 can be placed through and secured to the surrounding bodily tissues properly.

The coupling member 108 includes the first portion 118 and the second portion 120. The first portion 118 of the coupling member 108 is coupled to the distal end portion 112 of the first elongate member 104 and the second portion 120 of the coupling member 108 is coupled to the distal end portion 116 of the second elongate member 106 such that the first portion 118 of the coupling member 108 and the second portion 120 of the coupling member 108 are configured to be coupled together.

The first portion 118 of the coupling member 108 may include a male button. The second portion 120 of the coupling member 108 may include a female button. In some embodiments, the male and female buttons can be made of a polymeric material that may include a natural and/or a synthetic material. Exemplary polymeric materials are polypropylene, polyester, polyethylene, nylon, PVC, polystyrene, and the like. The male and female buttons are preferably made of a non-absorbable plastic material. In other embodiments the buttons may be made of biodegradable plastic material such as Polyglycolide (PGA), Polydioxanone (PDO) and the like.

The medical device 100 may further include a first suture and a second suture (not shown in FIG. 1). The first suture includes a proximal end portion and a distal end portion and the second suture also includes a proximal end portion and a distal end portion. The proximal end portion of the first suture is coupled to the first portion of the coupling member 108 and the distal end portion of the first suture is configured to be attached to a fourth bodily portion. The proximal end portion of the second suture is coupled to the second portion of the coupling member 108 and the distal end portion of the second suture is configured to be attached to a fifth bodily portion. In some embodiments, the fourth bodily portion and the fifth bodily portion is a sacrum of the patient. In some other embodiments the fourth bodily portion and the fifth bodily portion are other locations close to the sacrum. In some embodiments, the fourth bodily portion and the fifth bodily portion are same. In some other embodiments, the fourth bodily portion and the fifth bodily portion are different.

In some embodiments, the first suture and the second suture (together hereafter referred to as sutures) may be made of biological materials and/or synthetic materials. The sutures may be either absorbable (naturally biodegradable in the body) or non-absorbable. Exemplary absorbable sutures are polyglycolic acid, polylactic acid, polydioxanone, and the like. Exemplary non-absorbable sutures are nylon, polypropylene and the like. The biologic sutures can be made from biological materials, such as catgut suture, silk and the like. The sutures may be strong enough to hold the medical device securely and may also be flexible enough to be knotted.

In some embodiments, the first suture and the second suture are pulled toward sacrum or a portion of the sacrum with an appropriate tension thereby pulling the support member 102, the first elongate member 104, and the second elongate member 106 upward. This helps in lifting the prolapsed organs such as the anterior vaginal wall, posterior vaginal wall, cervix, and the uterus. An appropriate support is thus provided to the prolapsed organs by the medical device 100.

Figure 2:
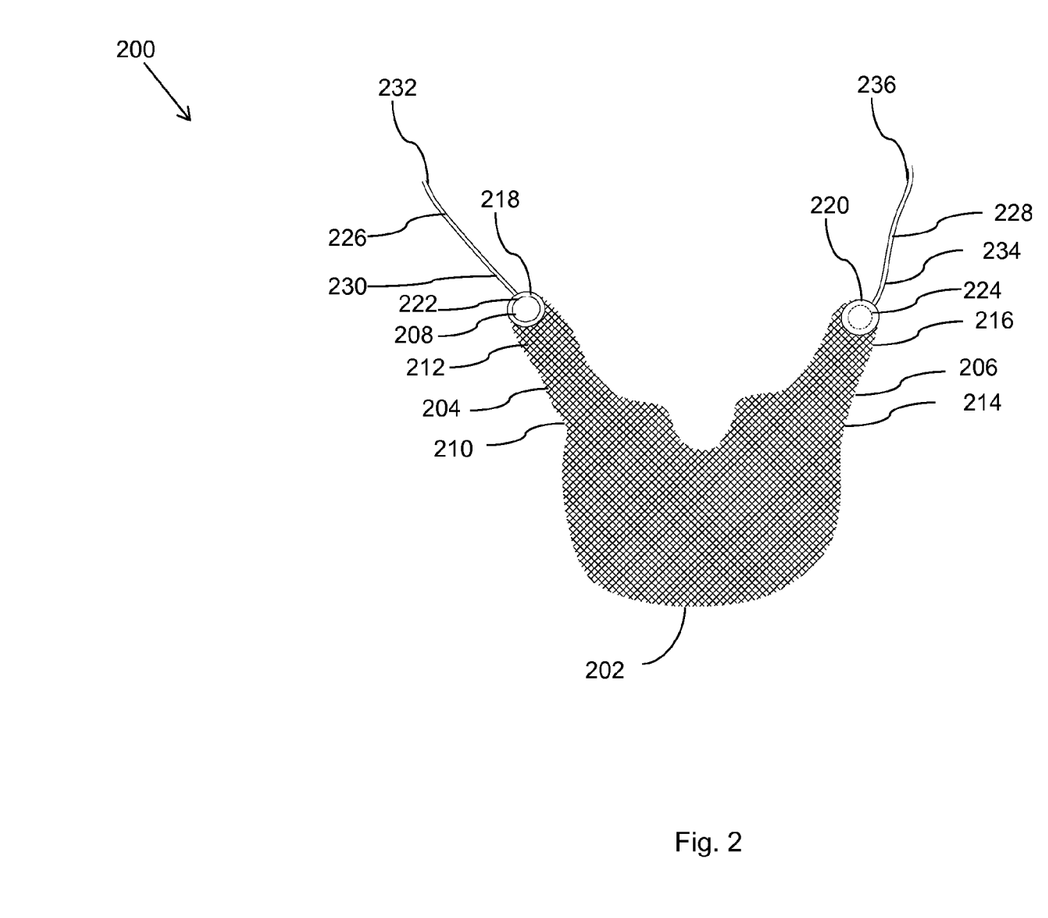
FIG. 2 is a perspective illustration of a medical device configured to be placed within a patient's body, in accordance with an embodiment of the present invention.

FIG. 2 is a perspective illustration of a medical device 200 configured to be delivered into a patient's body for the treatment of pelvic floor repair, in accordance with an embodiment of the present invention. The medical device 200 includes a support member 202, a first elongate member 204, a second elongate member 206, and a coupling member 208.

The support member 202 is configured to be placed within a patient's body such that the support member 202 is attached or stitched to a first bodily portion. In some embodiments, the first bodily portion is a portion of an anterior vaginal wall of the patient such that the support member 202 is attached or stitched to the portion of the anterior vaginal wall. In other embodiments, the first bodily portion is a portion of the posterior vaginal wall of the patient such that the support member 202 is attached or stitched to the portion of the posterior vaginal wall.

The support member 202 can be of a variety of different shapes, sizes, and configurations depending on the indented use of the medical device 200 and location of its placement within the body of the patient. In some embodiments, the support member 202 can be substantially rectangular, square, oval, or elliptical. The support member 202 can be shaped and sized in conformation to the portions of the vaginal walls of the patient where it is attached or stitched. In accordance with several embodiments, the support member 202 may be configured to conform to the shape of the body of the patient. For example, the support member 202 may be placed in a crescent shape, such as in the shape of a crescent moon, to help it conform to the anterior wall of the vagina.

The first elongate member 204 extends from the support member 202. The first elongate member 204 includes a proximal end portion 210 and a distal end portion 212 such that the proximal end portion 210 is attached to the support member 202 and the distal end portion 212 of the first elongate member 204 is configured to be attached around a second bodily portion. In some embodiments, the second bodily portion is a portion of a uterus of the patient such that the distal end portion 212 of the first elongate member 204 is wrapped around the portion of the uterus. In other embodiments, the second bodily portion is a portion of a cervix of the patient such that the distal end portion 212 of the first elongate member 204 is wrapped around the portion of the cervix.

The second elongate member 206 extends from the support member 202. The second elongate member 206 includes a proximal end portion 214 and a distal end portion 216 such that the proximal end portion 214 is attached to the support member 202 and the distal end portion 216 of the second elongate member 206 is configured to be attached around a third bodily portion. In some embodiments, the third bodily portion is a portion of a uterus of the patient such that the distal end portion 216 of the second elongate member 206 is wrapped around the portion of the uterus. In other embodiments, the third bodily portion is a portion of the cervix of the patient such that the distal end portion 216 of the second elongate member 206 is wrapped around the portion of the uterus. In some embodiments, the second bodily portion and the third bodily portion are same. In some other embodiments, the second bodily portion and the third bodily portion are different.

The first elongate member 204 and the second elongate member 206 can be of a variety of different shapes, sizes, and configurations depending on the indented use of the medical device 100 and location of its placement within the body of the patient. In some embodiments, the first elongate member 204 and the second elongate member 206 can be substantially planar, cylindrical, tubular, vasiform, cannular and the like. The first elongate member 204 and the second elongate member 206 can be shaped and sized to support the portion of the vaginal wall of the patient. In accordance with several embodiments, the first elongate member 204 and the second elongate member 206 may be configured to conform to the shape of the body of the patient. For example, the first and the second elongate members 204 and 206 may be placed in a cylindrical shape, such as in the shape of a hollow cylinder, to help it conform to and wrap around the cervix or the uterus of the patient.

In some embodiments, the first elongate member 204 and the second elongate member 206 are integral portions of the support member 202 such that the support member 202, the first elongate member 204 and the second elongate member 206 form a single integral structure. In other embodiments, the first elongate member 204 and the second elongate member 206 are removably or fixedly coupled to the support member 202. The first elongate member 204 and the second elongate member 206 may extend from any location of the support member 202 such that the medical device 200 comfortably supports and retains body portions of the patient. In some cases, the first elongated member 204 and the second elongated member 206 can be coupled to the support member 202 at two symmetric locations on either side of a central axis of the support member 202. In other cases, the first elongate member 204 and the second elongate member 206 can be coupled to the support member 202 at diametrically opposite locations.

In some embodiments, the support member 202, the first elongate member 204, and the second elongate member 206 are formed of a material that allows tissue in-growth after implantation. Various types of materials that can be employed to manufacture the support member 202, the first elongate member 204, and the second elongate member 206 have been described in conjunction with FIG. 1.

The support member 202, the first elongate member 204, and the second elongate member 206 can have a variety of sizes (length, width, and thickness) depending on the intended use of a particular medical device such as the medical device 200 and the intended site of implantation. For example, the size of the support member 202 can depend on the size of the vaginal wall. Similarly, the size of the first elongate member 204 and second elongate member 206 can have a length such that the support member 202 can be placed through and secured to the surrounding bodily tissues properly.

Figure 3A:
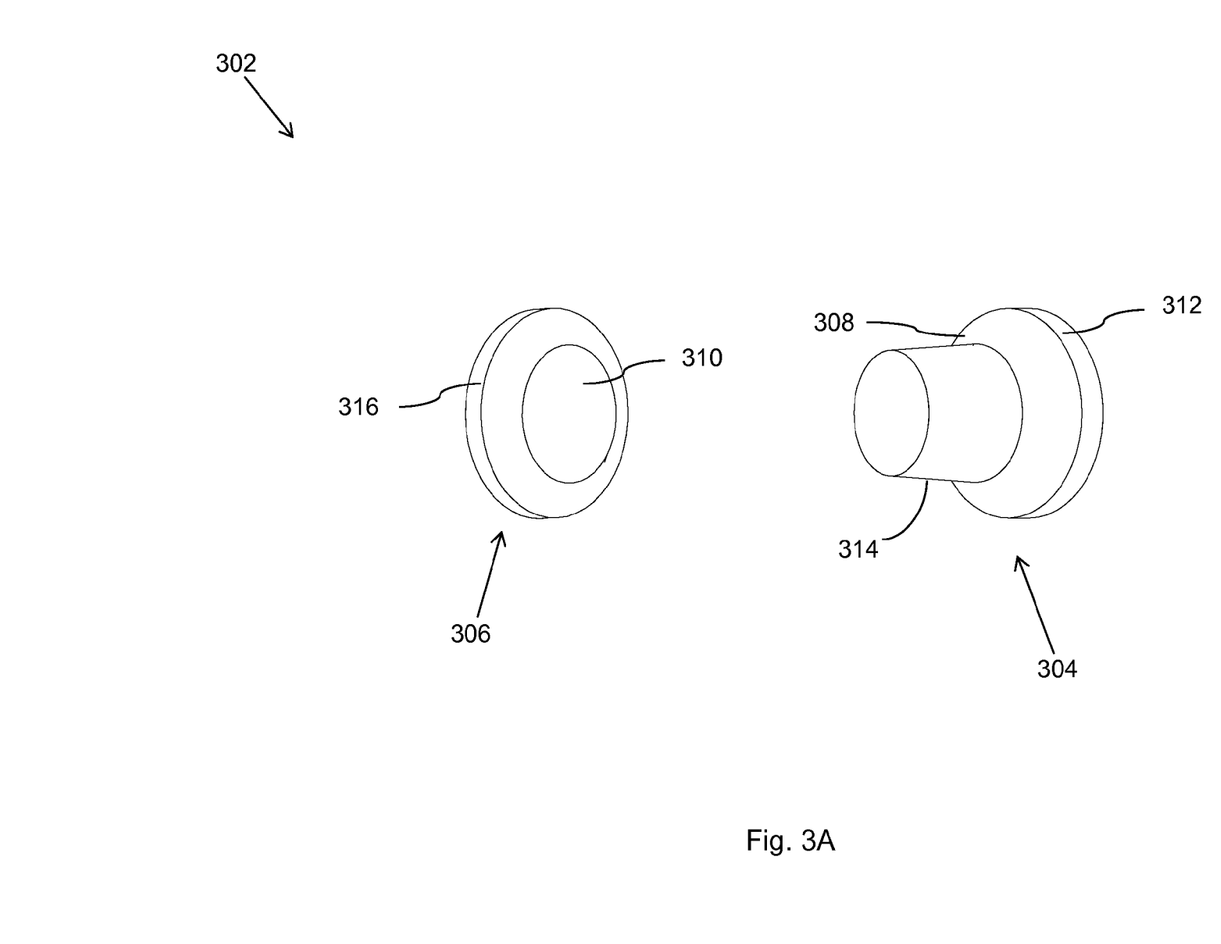
FIG. 3A is an enlarged view of a coupling member in a decoupled state, in accordance with an embodiment of the present invention.

The coupling member 208 includes a first portion 218 and a second portion 220. The first portion 218 of the coupling member 208 is coupled to the distal end portion 212 of the first elongate member 204 and the second portion 220 of the coupling member 208 is coupled to the distal end portion 216 of the second elongate member 206, wherein the first portion 218 of the coupling member 208 and the second portion 220 of the coupling member 208 are configured to be coupled together. The first portion 218 of the coupling member 208 includes a male button 222. The second portion 220 of the coupling member 208 includes a female button 224. The male button 222 of the coupling member 208 is configured to be plugged in to the female button 224 of the coupling member 208 thereby coupling the first elongate member 204 and the second elongate member 206 together. The male and female buttons 222 and 224 of the coupling member 208 are further described in conjunction with FIG. 3.

The medical device 200 also includes a first suture 226 and a second suture 228. The first suture 226 includes a proximal end portion 230 and a distal end portion 232 and the second suture 228 also includes a proximal end portion 234 and a distal end portion 236. The proximal end portion 230 of the first suture 226 is coupled to the first portion 218 of the coupling member 208 and the distal end portion 232 of the first suture 226 is configured to be attached to a fourth bodily portion. The proximal end portion 234 of the second suture 228 is coupled to the second portion 220 of the coupling member 208 and the distal end portion 236 of the second suture 228 is configured to be attached to a fifth bodily portion. In some embodiments, the fourth bodily portion and the fifth bodily portion is a sacrum of the patient. In some other embodiments, the fourth bodily portion and the fifth bodily portion can be any other location close to the sacrum. In some embodiments, the second bodily portion and the third bodily portion are same. In some other embodiments, the second bodily portion and the third bodily portion are different. The first suture 226 and the second suture 228 have also been discussed in conjunction with FIG. 1 in detail.

FIG. 3A illustrates an enlarged view of a coupling member 302 in a decoupled state in accordance with an embodiment of the present invention. The coupling member 302 includes a first portion 304 and a second portion 306. The first portion 304 of the coupling member 302 includes a male button 308. The second portion 306 of the coupling member includes a female button 310. The male button 308 includes a head portion 312 and a leg portion 314. The head portion 312 can be a disc or harrow shaped structure, and the like. The leg portion 314 is a cylindrical extension from the head portion 312.

Figure 3B:
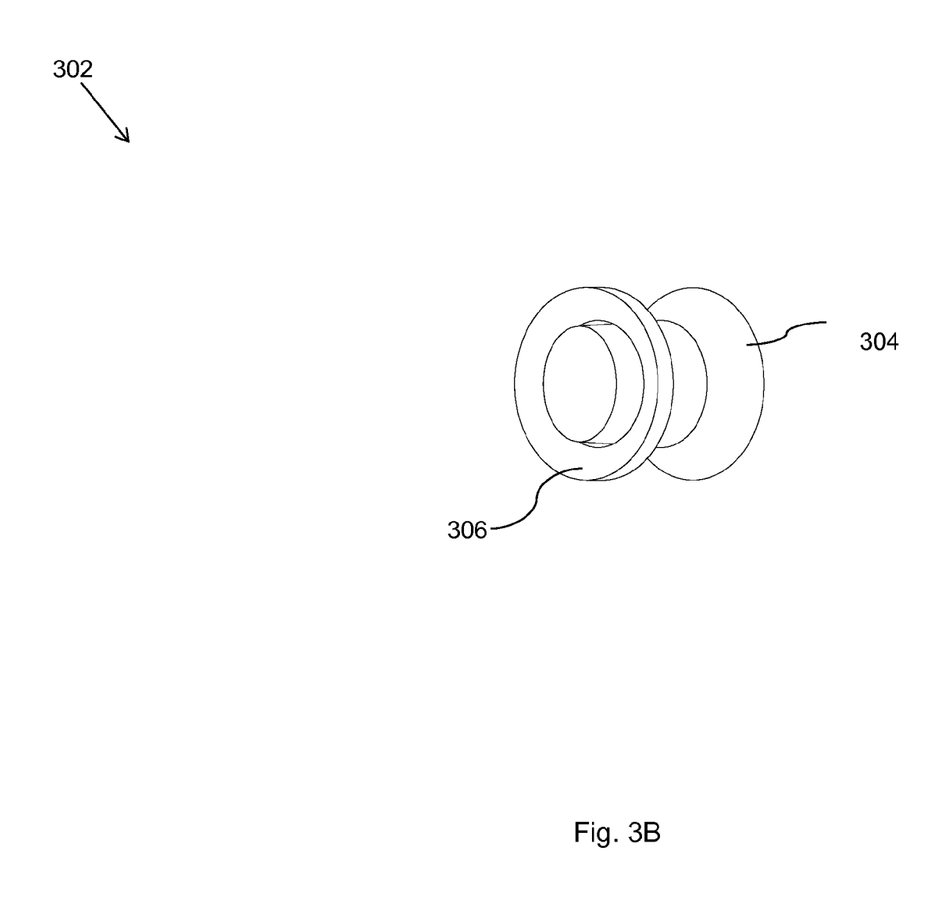
FIG. 3B is an enlarged view of the coupling member of FIG. 4A in a coupled state, in accordance with an embodiment of the present invention.

The female button 310 includes a head portion 316 such that the head portion 316 is a disc or harrow shaped structure, and the like. The head portion 316 of the female button 310 is hollow formed by inner peripheral surfaces of the female button 310. The cylindrical leg portion 314 of the male button 308 is capable of passing through the hollow portion formed by the inner peripheral surfaces of the female button 310. The male button 308 of the coupling member 302 and the female button 310 of the coupling member 302 are configured to be removably coupled together as illustrated in FIG. 4B. The male button 308 can be further pressed, thereby allowing the male button 308 to be fitted to the female button 310. In some embodiments, the removable coupling between the male button 308 of the coupling member 302 and the female button 310 of the coupling member 302 can be frictional fit or press fit which is achieved by friction after the parts are pushed together. The frictional or press fit can be achieved by pressing the two buttons 308 and 310 together against one another. In other embodiments, the removable coupling between the male button 308 of the coupling member 302 and the female button 310 of the coupling member 302 can be achieved through other mechanisms and fasteners such as springs, pins, and the like. In some embodiments, the coupling member 302 is a snap type coupling member.

The coupling member 202, first portion 204, and the second portion 206 as described above for coupling purposes is merely exemplary and it must be appreciated that various other types of coupling members as used in the conventional art can also be employed for the purposes of the present invention.

Figure 4A:
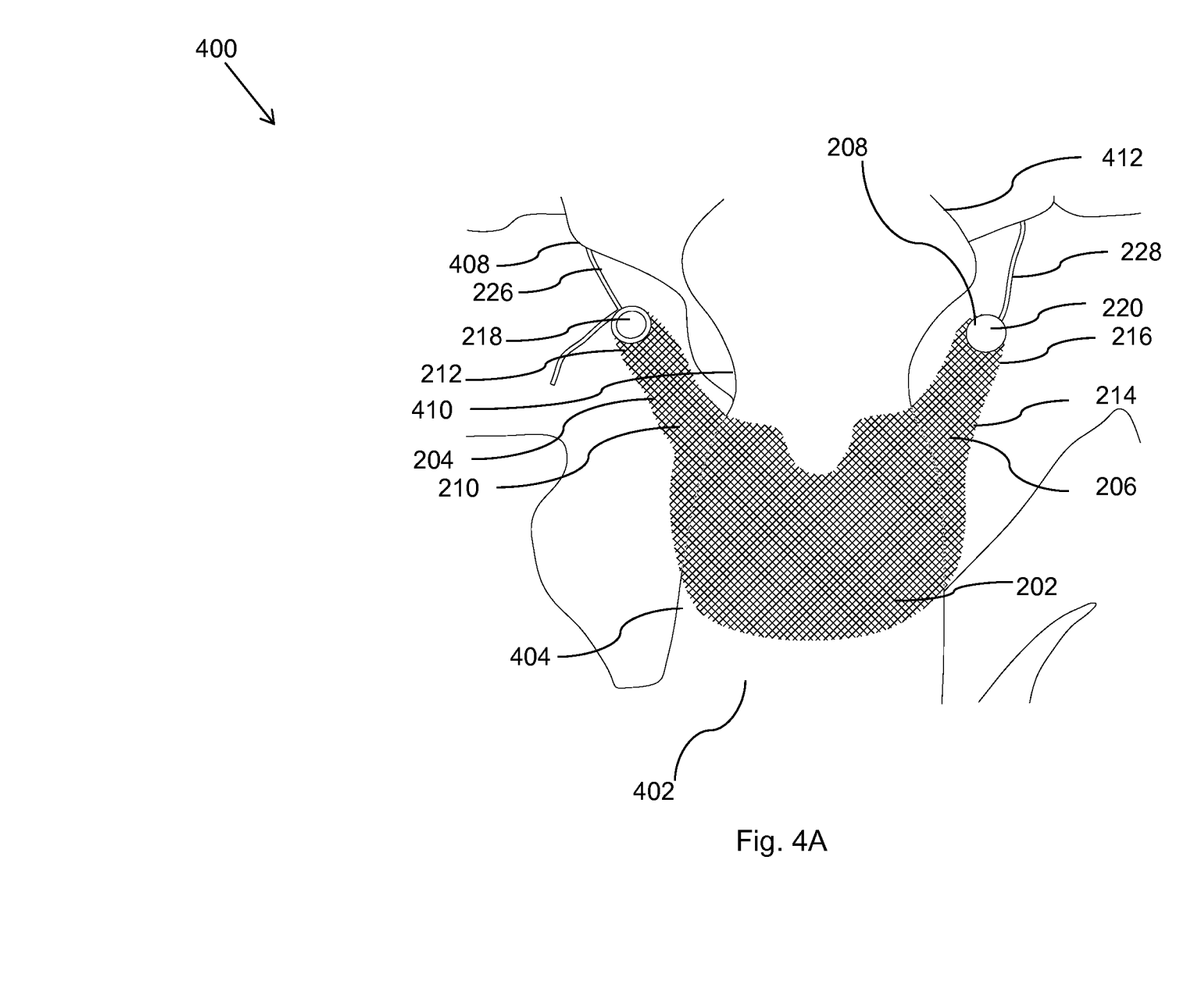
FIG. 4A illustrates placement of a medical device within a patient's body in a top view of a vaginal opening, in accordance with an embodiment of the present invention.
Figure 4B:
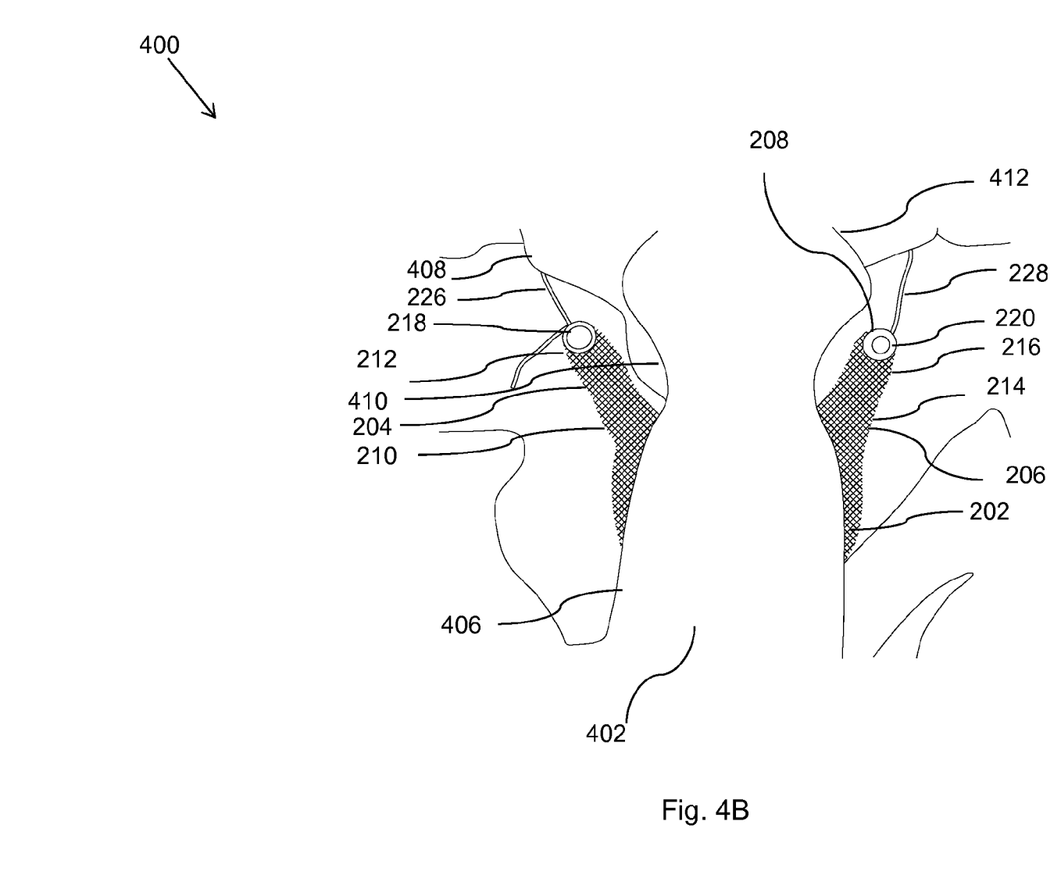
FIG. 4B illustrates placement of the medical device of FIG. 5A within a patient's body in a bottom view of a vaginal opening, in accordance with an embodiment of the present invention.
Figure 4C:
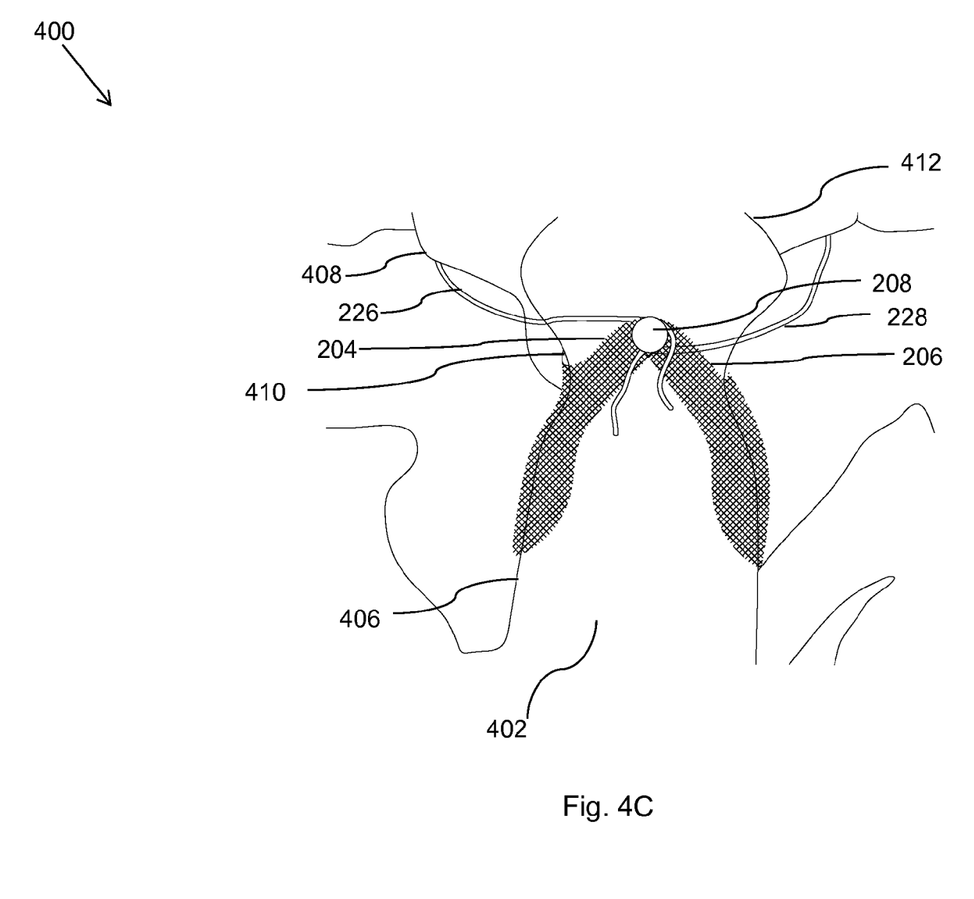
FIG. 4C illustrates placement of the medical device of FIG. 5A within a patient's body, with the coupling member in a coupled state, in accordance with an embodiment of the present invention.

FIG. 4A-4C illustrate perspective views of placement of the medical device 200 within a patient's body, in accordance with an embodiment of the present invention. FIG. 4A illustrates a view of placement from a top side of a vaginal opening. FIG. 4B illustrates a view of placement from a bottom side of the vaginal opening. FIG. 4C illustrates a view of placement with the coupling member 208 in a coupled state. The body portions of the patient such as a vagina (vaginal opening) 402, an anterior vaginal wall 404, a posterior vaginal wall 406, a sacrum 408, a cervix 410, and a uterus 412 are illustrated in FIGS. 4A-4C. The medical device 200 is hereafter used to describe the placement within the patient's body. However, other medical devices such as the medical device 100 may also be employed, in accordance with other embodiments of the present invention.

As illustrated, the support member 202 is attached or stitched to a portion of the anterior vaginal wall 404 of the patient. In other embodiments, the support member 202 may be attached or stitched to a portion of the posterior vaginal wall 406. In accordance with the illustrated embodiment, the support member 202 can be shaped and sized in conformation to the portion of the anterior vaginal wall 404 of the patient where it is attached or stitched. For example, the support member 202 may be placed in a crescent shape, such as in the shape of a crescent moon, to help it conform to the anterior vaginal wall 404. The first elongate member 204 extends from the support member 202. The proximal end portion 210 of the first elongate member 204 is attached to the support member 202 and the distal end portion 212 of the first elongate member 204 is attached around a portion of the uterus 412. The second elongate member 206 also extends from the support member 202. The proximal end portion 214 of the second elongate member 206 is attached to the support member 202 and the distal end portion 216 of the second elongate member 206 is attached around a portion of the uterus 412. Further, the proximal end portion 230 of the first suture 226 is coupled to the first portion 218 of the coupling member 208 and the distal end portion 232 of the first suture 226 is attached to the sacrum or close to the sacrum 408. The proximal end portion 234 of the second suture 228 is coupled to the second portion 220 of the coupling member 208 and the distal end portion 236 of the second suture 228 is attached to the sacrum or close to the sacrum 408.

Figure 5:
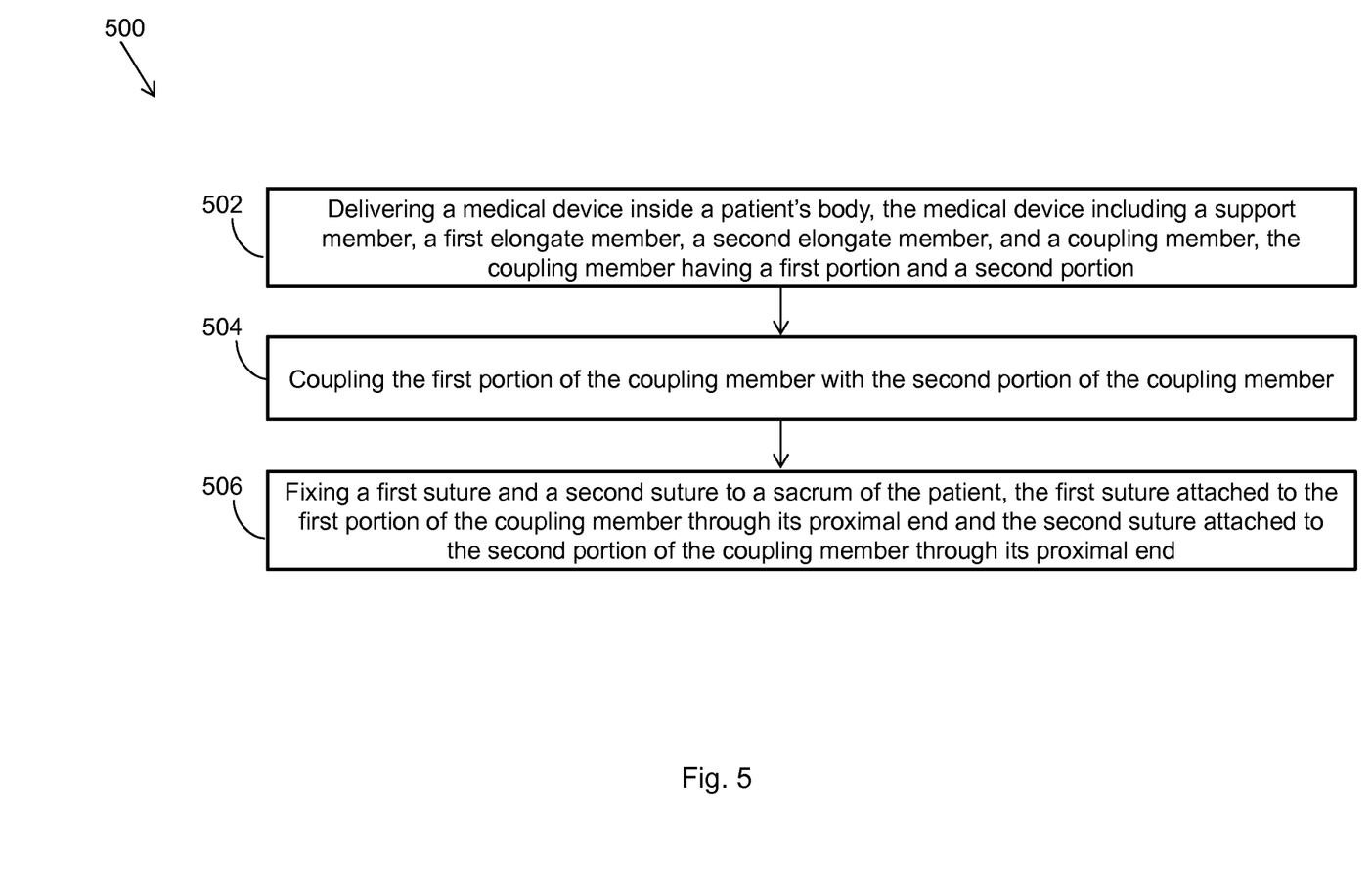
FIG. 5 is a flowchart illustrating a method of placing a medical device within a patient's body, in accordance with an embodiment of the present invention.

FIG. 5 is a flowchart illustrating a method 500 of placement of a medical device such as the medical device 100 or the medical device 200, in accordance with an embodiment of the present invention.

Referring now to FIG. 5 in conjunction with FIGS. 4A-4C, the method 500 of placement of the medical device 200 is described in accordance with an embodiment of the present invention. The medical device 200 is hereafter used to describe the placement in an exemplary embodiment. However, it must be appreciated that the medical device 100 may also be placed in the similar manner.

The method 500 includes delivering the medical device 200 inside the patient's body at step 502. The medical device 200 includes the support member 202, the first elongate member 204, and the second elongate member 206 extending from the support member 202. The medical device 200 further includes the coupling member 208 having the first portion 218 and the second portion 220. The medical device 200 has been described above in conjunction with FIG. 2. In some embodiments, an abdominal access may be crated to deliver the medical device 200 inside the patient's body. In other embodiments, a transvaginal access may be created for the delivery of the medical device 200. In accordance with various embodiments, an operator or a surgeon may make abdominal or vaginal incisions laproscopically, laprotomically, or in any other manner.

The method further includes coupling the first portion 218 of the coupling member 208 with the second portion 220 of the coupling member 208 at step 504. Coupling of the first portion 218 and the second portion 220 can be done through male and female buttons 222 and 224 as illustrated in FIGS. 2-3B. The male button 222 is configured to fit inside the female button 224. Various other coupling arrangements can also be used to couple the first portion 218 with the second portion 220.

After the medical device 200 is delivered and the first portion 218 is coupled with the second portion 220, the operator may wrap the first elongate member 204 and the second elongate member 206 around the cervix 410 or the uterus 412 or a portion of the cervix 410 or the uterus 412 of the patient. Thus, the wrapped elongate members 204 and 206 together with the support member 202 provide a desired support to the anterior and/or posterior vaginal walls 404 and 406 and the cervix or the uterus 410 and 412 of the patient. Similarly, any other prolapsed organ can be supported and lifted with the use of the medical device 200.

The method further includes fixing the first suture 226 and the second suture 228 to the sacrum 408 of the patient. As discussed in conjunction with FIG. 2 in detail, the first suture 226 is attached to the first portion 218 of the coupling member 208 through its proximal end and the second suture 228 is attached to the second portion 220 of the coupling member 208 through its proximal end. In order to ensure proper placement of the medical device 200 and proper fixation of the first suture 226 and the second suture 228, the medical device 200 may be pulled sufficiently to a defined anatomical location with the use of the first suture 226 and the second suture 228. The fixation of the sutures 226 and 228 to the sacrum 208 provides a desired tension to the support member 202.

In some embodiments, the sutures 226 and 228 are pulled toward sacrum 208 with an appropriate tension thereby pulling the support member 202, the first elongate member 204, and the second elongate member 206 upward. This helps in lifting the prolapsed organs such as the anterior vaginal wall 404, posterior vaginal wall 406, cervix 410, and the uterus 412. An appropriate support is thus provided to the prolapsed organs by the medical device 200.

It must be appreciated that the coupling of the first and second portion 218 and 220 of the coupling member 208 holds the first elongate member 204 and the second elongate member 206 together at the uterus or the cervix 412/410 but may not appropriately tension them. In some embodiments, it is through the first suture 226 and the second suture 228 that the tension capable of treating pelvic disorders is provided. In some embodiments, since the sutures 226 and 228 are very thin as compared to the width of the elongate members 204 and 206, therefore they can be passed through anatomical locations from the vaginal walls 404 and 406 to the sacrum 408 easily. Therefore, removal of the uterus 412 is avoided through the disclosed surgical procedure.

In some embodiments, a medical device configured to be delivered and placed within a patient's body includes a support member, a first elongate member, a second elongate member and a coupling member. The support member is configured to be attached to a portion of a vaginal wall. The first elongate member extends from the support member, the first elongate member having a proximal end portion and a distal end portion such that the proximal end portion is attached to the support member and the distal end portion of the first elongate member being configured to be attached around a portion of a uterus. The second elongate member extending from the support member, the second elongate member having a proximal end portion and a distal end portion such that the proximal end portion is attached to the support member and the distal end portion of the second elongate member being configured to be attached around a portion of the uterus. The coupling member having a first portion and a second portion, the first portion of the coupling member coupled to the distal end portion of the first elongate member and the second portion of the coupling member coupled to the distal end portion of the second elongate member, wherein the first portion of the coupling member and the second portion of the coupling member are configured to be coupled together.

In some embodiments, the medical device is a bodily implant configured to treat uterine prolapse. In some embodiments, the support member includes a mesh configured to be stitched to the portion of the vaginal wall. In some embodiments, the vaginal wall is an anterior vaginal wall of the patient such that the support member is configured to be stitched to the anterior vaginal wall. In some embodiments, the coupling member is made of a plastic. In some embodiments, the plastic is polypropylene. In some embodiments, the coupling member is made of a biodegradable material. In some embodiments, the first portion of the coupling member includes a male button. In some embodiments, the second portion of the coupling member includes a female button. In some embodiments, the coupling member is made of a non-absorbable plastic. In some embodiments, the coupling member is made of a biodegradable material.

In some embodiments, the device includes a first suture having a proximal end portion and a distal end portion, wherein the proximal end portion of the first suture is coupled to the first portion of the coupling member and the distal end portion of the first suture is configured to be attached to a portion of a sacrum of the patient.

In some embodiments, the device includes a second suture having a proximal end portion and a distal end portion, wherein the proximal end portion of the second suture is coupled to the second portion of the coupling member and the distal end portion of the second suture is configured to be attached to a portion of the sacrum of the patient.

In some embodiments, a method of placing a medical device in a patient's body, includes delivering the medical device inside the patient's body, the medical device having a support member configured to be attached to a portion of a vaginal wall, a first elongate member and a second elongate member extending from the support member and configured to be attached around a portion of a uterus, a coupling member having a first portion and a second portion, the first portion of the coupling member coupled to the first elongate member and the second portion of the coupling member coupled to the second elongate member; coupling the first portion of the coupling member with the second portion of the coupling member; and fixing a first suture and a second suture to a sacrum of the patient, the first suture attached to the first portion of the coupling member through its proximal end and the second suture attached to the second portion of the coupling member through its proximal end.

In some embodiments, the method includes creating an access to a vagina for delivery of the medical device. In some embodiments, the access is created transvaginally.

In some embodiments, the method includes stitching the support member to the portion of the vaginal wall. In some embodiments, the vaginal wall is an anterior vaginal wall.

In some embodiments, the method includes pulling the medical device to a defined anatomical location with the use of the first suture and the second suture. In some embodiments, the medical device is a bodily implant configured to treat uterine prolapse.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device configured to be delivered and placed within a patient's body, the medical device comprising:
    a support member configured to be attached to a portion of a vaginal wall;
    a first elongate member extending from the support member, the first elongate member having a proximal end portion and a distal end portion such that the proximal end portion is attached to the support member and the distal end portion of the first elongate member being configured to be attached around a portion of a uterus;
    a second elongate member extending from the support member, the second elongate member having a proximal end portion and a distal end portion such that the proximal end portion is attached to the support member and the distal end portion of the second elongate member being configured to be attached around a portion of the uterus;
    a coupling member having a first portion and a second portion, the first portion of the coupling member coupled to the distal end portion of the first elongate member and the second portion of the coupling member coupled to the distal end portion of the second elongate member, wherein the first portion of the coupling member and the second portion of the coupling member are configured to be directly coupled together such that the distal end portion of the first elongate member is coupled to the distal end portion of the second elongate member;
    a first suture coupled to the first portion of the coupling member on the first elongate member; and
    a second suture coupled to the second portion of the coupling member on the second elongate member,
    wherein, when the first portion of the coupling member is directly coupled to the second portion of the coupling member, the first suture and the second suture are each configured to extend from the coupling member to different portions of bodily tissue within the patient's body.

2. The medical device of claim 1, wherein the medical device is a bodily implant configured to treat uterine prolapse.

3. The medical device of claim 1, wherein the support member includes a mesh configured to be stitched to the portion of the vaginal wall.

4. The medical device of claim 1, wherein the vaginal wall is an anterior vaginal wall of the patient such that the support member is configured to be stitched to the anterior vaginal wall.

5. The medical device of claim 1, wherein the coupling member is made of a plastic.

6. The medical device of claim 5, wherein the plastic is polypropylene.

7. The medical device of claim 1, wherein the coupling member is made of a biodegradable material.

8. The medical device of claim 1, wherein the first portion of the coupling member is a male button, and the second portion of the coupling member is a female button.

9. The medical device of claim 1, wherein the second portion of the coupling member defines an opening, and the first portion of the coupling member is configured to be inserted into the opening of the second portion of the coupling member.

10. The medical device of claim 1, wherein the first and second elongate members are coupled to the support member at two symmetric locations with respect to a central axis of the support member.

11. The medical device of claim 1, wherein the first portion of the coupling member includes a head portion having a disc shape, the first portion of the coupling member including a leg portion, the leg portion being a cylindrical extension from the head portion, the second portion of the coupling member having a head portion defining a cavity formed by inner peripheral surfaces of the second portion of the coupling member.

12. The medical device of claim 1, wherein the first suture includes a proximal end portion and a distal end portion, wherein the proximal end portion of the first suture is coupled to the first portion of the coupling member and the distal end portion of the first suture is configured to be attached to a portion of a sacrum of the patient.

13. The medical device of claim 12, wherein the second suture includes a proximal end portion and a distal end portion, wherein the proximal end portion of the second suture is coupled to the second portion of the coupling member and the distal end portion of the second suture is configured to be attached to another portion of the sacrum of the patient.

14. A method of placing a medical device in a patient's body, the method comprising:
   delivering the medical device inside the patient's body, the medical device having a support member configured to be attached to a portion of a vaginal wall, a first elongate member and a second elongate member extending from the support member and configured to be attached around a portion of a uterus, a coupling member having a first portion and a second portion, the first portion of the coupling member coupled to the first elongate member and the second portion of the coupling member coupled to the second elongate member, the medical device having a first suture coupled to the first portion of the coupling member, and a second suture coupled to the second portion of the coupling member;
   directly coupling the first portion of the coupling member with the second portion of the coupling member such that a distal end portion of the first elongate member is coupled to a distal end portion of the second elongate member, the first and second sutures extending from the coupling member from a portion of a uterus of the patient; and
   extending the first and second sutures from the portion of the uterus to different portions of a sacrum of the patient including,
      extending the first suture to a first portion of the sacrum of the patient; and
      extending the second suture to a second portion of the sacrum of the patient.

15. The method of claim 14 further comprising creating an access to a vagina for delivery of the medical device.

16. The method of claim 15, wherein the access is created transvaginally.

17. The method of claim 14, further comprising stitching the support member to the portion of the vaginal wall.

18. The method of claim 14, wherein the vaginal wall is an anterior vaginal wall.

19. The method of claim 14 further comprising pulling the medical device to a defined anatomical location with use of the first suture and the second suture.

20. The method of claim 14, wherein the medical device is a bodily implant configured to treat uterine prolapse.

* * * * *